United States Patent
Garcia-Bengochea et al.

(10) Patent No.: US 9,526,554 B2
(45) Date of Patent: Dec. 27, 2016

(54) SYSTEM, INSTRUMENTATION AND METHOD FOR SPINAL FIXATION USING MINIMALLY INVASIVE SURGICAL TECHIQUES

(76) Inventors: Javier Garcia-Bengochea, Jacksonville, FL (US); Andrew F. Cannestra, Jacksonville, FL (US)

(*) Notice: Subject to any disclaimer, the term of this patent is extended or adjusted under 35 U.S.C. 154(b) by 78 days.

(21) Appl. No.: 12/931,976

(22) Filed: Feb. 15, 2011

(65) Prior Publication Data
US 2011/0144652 A1    Jun. 16, 2011

Related U.S. Application Data

(63) Continuation of application No. 12/315,546, filed on Dec. 4, 2008.

(60) Provisional application No. 61/005,323, filed on Dec. 4, 2007.

(51) Int. Cl.
*A61B 17/70*     (2006.01)
*A61B 17/88*     (2006.01)

(52) U.S. Cl.
CPC ....... *A61B 17/8897* (2013.01); *A61B 17/7002* (2013.01); *A61B 17/7083* (2013.01)

(58) Field of Classification Search
CPC . A61B 17/02–17/0293; A61B 17/70–17/7046; A61B 17/7083–17/7092; A61B 17/7076–17/7082
USPC .............. 606/86 R, 86 A, 99, 103, 246, 279
See application file for complete search history.

(56) References Cited

U.S. PATENT DOCUMENTS

| | | | |
|---|---|---|---|
| 6,821,277 B2 | 11/2004 | Teitelbaum | |
| 7,179,261 B2 | 2/2007 | Sicvol et al. | |
| 7,188,626 B2 | 3/2007 | Foley et al. | |
| 7,250,052 B2 | 7/2007 | Landry et al. | |
| 7,648,521 B2* | 1/2010 | Hestad | 606/246 |
| 8,043,343 B2* | 10/2011 | Miller et al. | 606/279 |
| 8,298,139 B2* | 10/2012 | Hamada | A61B 17/02 600/233 |
| 2005/0065517 A1* | 3/2005 | Chin | A61B 17/3421 606/86 A |
| 2005/0080418 A1* | 4/2005 | Simonson et al. | 606/61 |
| 2005/0131421 A1* | 6/2005 | Anderson et al. | 606/99 |
| 2005/0277812 A1* | 12/2005 | Myles | A61B 17/0293 600/231 |
| 2005/0277934 A1* | 12/2005 | Vardiman | 606/61 |
| 2006/0036255 A1* | 2/2006 | Pond et al. | 606/86 |
| 2007/0049931 A1* | 3/2007 | Justis | A61B 17/7089 606/86 A |
| 2007/0299444 A1* | 12/2007 | DiPoto et al. | 606/61 |
| 2008/0015582 A1* | 1/2008 | DiPoto et al. | 606/61 |
| 2008/0140120 A1* | 6/2008 | Hestad et al. | 606/246 |
| 2008/0140132 A1* | 6/2008 | Perez-Cruet | 606/301 |

* cited by examiner

*Primary Examiner* — Jan Christopher Merene
*Assistant Examiner* — Steven Cotroneo
(74) *Attorney, Agent, or Firm* — Thomas C. Saitta

(57) ABSTRACT

A pedicle screw tower having a guide chute, open at both ends, affixed to the exterior of the main body of the tower. The guide chute extends the length of the tower and is curved inwardly at its bottom such that the exit direction is at approximately 90 degrees to and facing the central axis of tower. A guide cable is passed into and through the guide chute such that it is directed across the tower to an adjacent tower.

12 Claims, 1 Drawing Sheet

SYSTEM, INSTRUMENTATION AND METHOD FOR SPINAL FIXATION USING MINIMALLY INVASIVE SURGICAL TECHIQUES

This application is a continuation of U.S. patent application Ser. No. 12/315,546, filed Dec. 4, 2008, now abandoned, claiming the benefit of U.S. Provisional Patent Application Ser. No. 61/005,323, filed Dec. 4, 2007, the disclosures of both of which are incorporated herein by reference.

BACKGROUND OF THE INVENTION

This invention relates generally to the field of systems, instrumentation and methodology for the fixation of vertebrae relative to each other, and more particularly relates to such systems, instrumentation and methodology that utilize pedicle screws affixed to vertebral pedicles and one or more rods that rigidly join the pedicle screws of plural vertebrae. The invention contemplates the combination and use of plural pedicle screws, one or more rods and means to optimize insertion of the rod into the pedicle screws, such means comprising a guide cable and instrumentation to position the guide cable in the pedicle screws, whereby the screws are implanted into the vertebrae, the guide cable positioned in the screws and the rod subsequently guided into the pedicle screws along the guide cable, all using minimally invasive surgical incisions. With regard to instrumentation of the invention, the invention relates to guide cable threading or advancing devices adapted to pass the guide cable from one pedicle screw to an adjacent pedicle screw.

Early surgical techniques for affixing rods to vertebrae entailed relatively long incisions to provide access to the vertebrae. Newer techniques utilize multiple percutaneous stab incisions at chosen locations rather than a single long incision. Such techniques are often referred to as minimally invasive surgery (MIS). The MIS techniques are preferable with regard to recovery time.

One advanced MIS technique provides for the placement and passing of a guide cable or wire between the pedicle screws such that the guide cable can be utilized to direct and/or pull a fixation rod into proper position spanning the pedicle screws. Inserting the guide cable into the first pedicle screw tower and then through the tissue between the pedicle screws can be a difficult and time-consuming task. It is an object of this invention therefore to provide structure for a pedicle screw tower that greatly reduces the difficulty in this task.

SUMMARY OF THE INVENTION

The invention comprises in general an improved pedicle screw tower and method of using the tower in conjunction with the combination and use of plural pedicle screws implanted into vertebrae, screw extenders or towers extending from the pedicle screws to provide access to the heads of the screws, one or more rods for connecting the pedicle screws in a relatively rigid manner to prevent undesirable movement of the vertebrae, wherein a guide cable is inserted and positioned between the heads of the pedicle screws to guide the rod into proper position bridging the pedicle screws, all using minimally invasive surgical incisions. The pedicle screw tower is structured for use as the first of a series of pedicle screw towers, the first pedicle screw tower being the tower into which a guide cable is first inserted. The first tower comprises a guide chute, open at both ends, affixed to the exterior of the main body of the tower. The guide chute extends the length of the tower and is curved at its bottom such that the exit direction is at approximately 90 degrees to the central axis of tower.

DETAILED DESCRIPTION OF THE INVENTION

Figure 1:
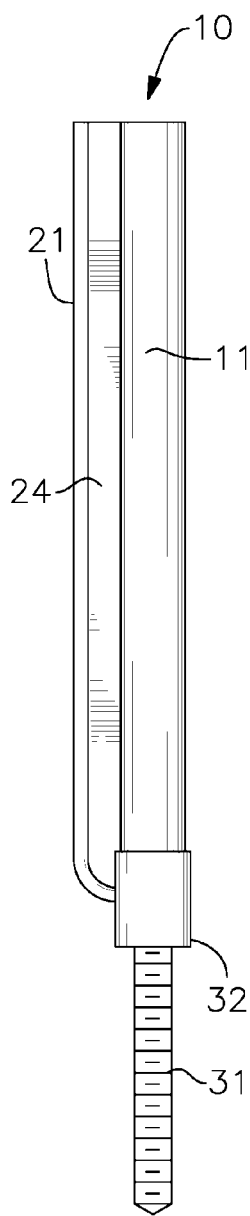
FIG. 1 is a side view of an embodiment of the invention showing the tower mounted onto a pedicle screw.

With reference to the drawings the invention will now be described in detail with regard for the best mode and the preferred embodiment. The invention comprises in general an pedicle screw guide tower and method of using the tower in conjunction with the combination and use of plural pedicle screws 31 implanted into vertebrae, screw extenders or towers extending from the pedicle screws 31 to provide access to the heads 32 of the screws 31, one or more rods for connecting the pedicle screws 31 in a relatively rigid manner to prevent undesirable movement of the vertebrae, wherein a guide cable or wire is inserted and positioned between the heads 32 of the pedicle screws 31 to guide the rod into proper position bridging the pedicle screws 31, all using minimally invasive surgical incisions.

Pedicle fixation is accomplished by creating multiple percutaneous incisions, as opposed to an open or long incision, often referred to as stab incisions. The percutaneous incisions allow for pedicle screws 31 to be inserted into each desired vertebra by cutting or making a short incision, drilling into the vertebra and inserting a pedicle screw 31. Screw extenders or towers are connected to the pedicle screws 31, the towers having slotted sides to provide access to their interiors. The guided cable, preferably a braided member composed of stainless steel or titanium, is passed into the first tower 10 and down to the head 32 of the pedicle screw.

Figure 2:
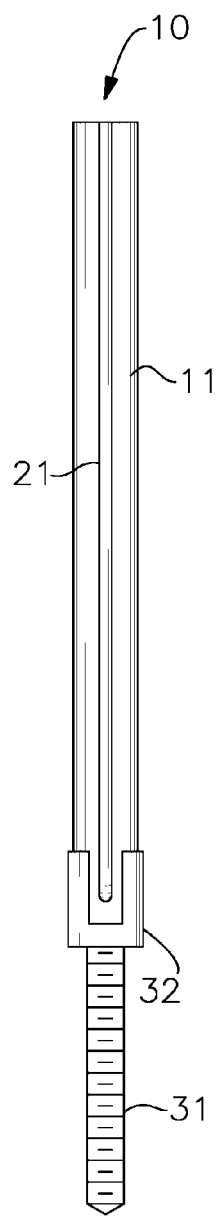
FIG. 2 is a rear view of the tower of FIG. 1.
Figure 3:
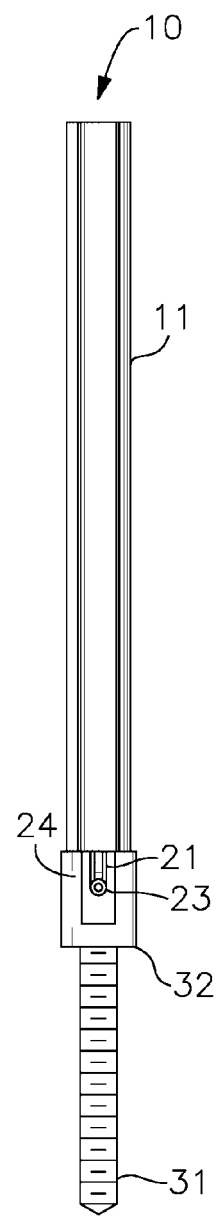
FIG. 3 is a front view of the tower of FIG. 1.
Figure 4:
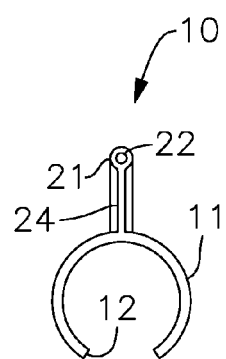
FIG. 4 is a top view of the guide tower of FIG. 1.

The pedicle screw tower 10 of the invention, shown in FIGS. 1 through 4, comprises an elongated, generally tubular main body 11, open on both ends and with an axially extending slot 12 preferably extending the entire length of the main body 11. the axial slot 12 allows for greater manipulation of instrumentation within the tower 10. The tower 10 is constructed suach that it may be connected in known manner to the head 32 of the pedicle screw 31. An elongated guide chute 21 is mounted onto the exterior of the main body 11 opposite to axial slot 12, preferably with a mounting flange 24 extending the full length of the main body 11. The majority of the length of the guide chute 21 extends parallel to the central axis of the main body 11. The guide chute 21 is hollow and has a top opening 22 located at or near the top of the main body 11 and a bottom opening 23 located at the bottom end of the guide chute 21. The bottom end of the guide chute 21 is bent in a curved manner approximately 90 degrees from the axial direction, such that the bottom opening 22 faces laterally. The bottom opening 22 faces the interior of the main body 11, and most preferably is aimed directly at a point on the central axis of the main body 11. The tower 10 is aligned with the slotted pedicle screw head 32 such that the axial slot 12 aligns with a slot in the head 32.

To utilize the tower 10, a guide cable is inserted into the top opening 22 and pushed into and through the bottom opening 23. Because the bottom opening 23 is facing inwardly at 90 degrees, the guide cable exits the bottom opening 23 transversely to the axial direction. In this manner the direction of travel of the guide cable has been changed from axial to lateral, and continued insertion of the guide cable into the guide chute 21 causes the end of the guide cable to pass across and through the slot of the pedicle head 32. The pedicle screws 31 and towers 10 are appropriately aligned such that the guide wire travels to the adjacent pedicle screw 31 and its associated tower. Once the guide cable enters the second tower it can be grasped using forceps or similar equipment and pulled from the second tower to advance the guide cable.

Once the cable has been properly positioned in the heads of the pedicle screws 31, it is finally brought out through a percutaneous incision at an offset or displaced location, or alternatively brought out through the last tower. A cannulated or tubular rod is then inserted over the free end of the cable and passed down the cable through the offset incision using a rod insertion instrument. The rod is preferably malleable in vivo to account for torque imparted by the set screws used to secure the rod to the pedicle screws 31. After the rod is properly positioned, the rod is affixed or secured to the pedicle screws 31 in standard manner, the cable is cut or withdraw and the screw towers are removed.

It is understood that equivalents and substitutions for elements set forth above may be obvious to those of ordinary skill in the art, and therefore the true scope and definition of the invention is to be as set forth in the following claims.

We claim:

1. A pedicle screw tower comprising:
   a tubular, elongated main body, open at both ends and comprising an axial slot, said main body defining a central axis;
   a hollow guide chute comprising a top opening isolated from and not in direct communication with said ends of said main body, and a bottom opening in direct communication with said main body, said guide chute open only at said top and bottom openings, said guide chute affixed to said main body and having a diameter smaller than the diameter of said main body, said guide chute defining a bore having an upper portion parallel to, isolated from and not in direct communication with said main body and a lower portion curved at its bottom approximately 90 degrees toward the central axis of said main body and in direct communication with said main body through said bottom opening, such that said bore provides a passageway from said top opening through said bottom opening into said main body, whereby a guide cable inserted into said top opening, through said bore and past said bottom opening passes across said main body and through said axial slot.

2. The tower of claim 1, wherein said guide chute is positioned externally to said main body and is affixed to the exterior of said main body with a mounting flange extending between said guide chute and said main body.

3. The tower of claim 2, wherein said mounting flange is aligned parallel to said central axis of said main body.

4. The tower of claim 1, wherein said guide chute extends the full length of said main body.

5. The tower of claim 1, wherein said bottom opening faces transverse to the central axis of said main body.

6. The tower of claim 1, further whereby said guide chute is adapted to receive a guide cable inserted axially into said top opening and extending laterally from said bottom opening.

7. The tower of claim 1, wherein said axial slot extends the full length of said main body.

8. A method of advancing a guide cable through a first pedicle screw tower comprising the steps of:
   providing a tubular, elongated main body, open at both ends and comprising an axial slot, said main body defining a central axis and a main body passageway; and a hollow guide chute having a diameter smaller than the diameter of said main body and comprising a top opening, a bottom opening and a bore extending from said top opening to said bottom opening, said guide chute positioned externally to said main body, said bore having an upper portion parallel to said central axis of said main body and a lower portion curved at its bottom approximately 90 degrees toward the central axis of said main body, said bore defining a bore passageway extending from said top opening through said bottom opening into said main body, wherein said bore passageway is isolated from said main body passageway except at said bottom opening;
   connecting said tower to a pedicle screw; and
   inserting a guide cable into said top opening and advancing said guide cable through said guide chute and out from said bottom opening into said main body and toward and across said central axis and then out from said main body through said axial slot.

9. The method of claim 8 further comprising the steps of:
   providing a second pedicle screw tower connected to a second pedicle screw;
   further advancing said guide cable from said pedicle screw tower into said second pedicle screw tower; and
   grasping said guide cable within said second pedicle tower and pulling said guide cable from said second pedicle screw tower.

10. A pedicle screw tower comprising:
    a tubular, elongated main body, open at both ends and comprising an axial slot, said main body defining a central axis and a main body passageway;
    a hollow guide chute having a diameter smaller than the diameter of said main body and comprising a top opening, a bottom opening and a bore extending from said top opening to said bottom opening, said guide chute positioned externally to said main body, said bore having an upper portion parallel to said central axis of said main body and a lower portion curved at its bottom approximately 90 degrees toward the central axis of said main body, said bore defining a bore passageway extending from said top opening through said bottom opening into said main body, wherein said bore passageway is isolated from said main body passageway except at said bottom opening.

11. The tower of claim 10, wherein said guide chute is affixed to the exterior of said main body with a mounting flange aligned parallel to said central axis of said main body.

12. The tower of claim 10, further whereby said guide chute is adapted to receive a guide cable inserted axially into said top opening and extending laterally from said bottom opening into said main body.

* * * * *